United States Patent
Sommer et al.

(10) Patent No.: US 7,953,495 B2
(45) Date of Patent: May 31, 2011

(54) LEAD-IMPLANT COUPLING DEVICE

(75) Inventors: John L. Sommer, Coon Rapids, MN (US); Michael D. Eggen, Lake Elmo, MN (US); Joseph A. DuPay, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 474 days.

(21) Appl. No.: 12/112,095

(22) Filed: Apr. 30, 2008

(65) Prior Publication Data
US 2009/0276002 A1 Nov. 5, 2009

(51) Int. Cl.
*A61N 1/04* (2006.01)

(52) U.S. Cl. .......... 607/116; 607/115; 607/36; 607/122; 493/909; 600/373; 600/374; 600/585

(58) Field of Classification Search ............ 607/37, 607/30, 32; 606/35–41
See application file for complete search history.

(56) References Cited

U.S. PATENT DOCUMENTS

| | | | |
|---|---|---|---|
| 3,683,932 A | 8/1972 | Cole | |
| 3,871,382 A | 3/1975 | Mann | |
| 3,908,668 A * | 9/1975 | Bolduc | 607/37 |
| 4,106,512 A | 8/1978 | Bisping | |
| 4,135,518 A | 1/1979 | Dutcher | |
| 4,278,093 A | 7/1981 | Lafortune et al. | |
| 4,311,153 A | 1/1982 | Smits | |
| 4,402,329 A | 9/1983 | Williams | |
| 5,697,804 A * | 12/1997 | Froberg et al. | 439/346 |
| 5,741,321 A | 4/1998 | Brennen | |
| 6,269,270 B1 | 7/2001 | Boveja | |
| 6,335,492 B1 | 1/2002 | Terasaka et al. | |
| 7,103,414 B1 * | 9/2006 | Poore et al. | 607/32 |
| 7,289,855 B2 | 10/2007 | Nghiem et al. | |
| 7,512,446 B2 * | 3/2009 | Honeck | 607/116 |
| 7,753,696 B2 * | 7/2010 | Hoecke et al. | 439/92 |
| 2002/0183819 A1 * | 12/2002 | Struble | 607/122 |
| 2003/0068914 A1 | 4/2003 | Merry et al. | |
| 2004/0147822 A1 | 7/2004 | Al-Ali et al. | |
| 2004/0199212 A1 * | 10/2004 | Fischell et al. | 607/32 |
| 2004/0230267 A1 | 11/2004 | Wenger | |
| 2005/0103351 A1 * | 5/2005 | Stomberg et al. | 128/898 |
| 2006/0144747 A1 | 7/2006 | Le et al. | |
| 2007/0123947 A1 | 5/2007 | Wenger et al. | |
| 2007/0173900 A1 | 7/2007 | Siegal et al. | |
| 2008/0255630 A1 * | 10/2008 | Arisso et al. | 607/37 |

FOREIGN PATENT DOCUMENTS
WO 2008017059 2/2008

OTHER PUBLICATIONS

International Search Report, PCT/US2009/039400, 3 pages, Feb. 2, 2008.

* cited by examiner

*Primary Examiner* — Carl H Layno
*Assistant Examiner* — Paula J Stice
(74) *Attorney, Agent, or Firm* — Stephen W. Bauer; Reed A. Duthler (57) ABSTRACT

A lead coupling device adapted for coupling to a lead and methods for using the coupling devices are provided. The coupling device includes a housing assembly having a proximal opening and a distal opening. The coupling device also has a lead receiving channel that is disposed between the two openings to receive a lead therethrough. Various electronics components may also included in the coupling device that enable operations such as sensing, delivery of electrical energy and wireless communication between the coupling device and an external device.

14 Claims, 7 Drawing Sheets

LEAD-IMPLANT COUPLING DEVICE

TECHNICAL FIELD

The present disclosure generally relates to implantable medical devices. More specifically and without limitation, the present disclosure relates to leads for implantable medical devices.

CROSS REFERENCE TO RELATED APPLICATION

Reference is made to commonly-assigned and co-pending application U.S. Ser. No. 12/112,111, filed on Apr. 30, 2008, entitled "Lead Implant System;" U.S. Ser. No. 12/112,102, filed Apr. 30, 2008, entitled "Remote Lead-Implant Coupling Device;" and U.S. Ser. No. 12/112,090, Apr. 30, 2008, entitled "Medical Device Packaging Systems Including Electrical Interfaces," all of which are herein incorporated by reference in their entirety.

BACKGROUND

In general, implantable medical devices are commonly used with medical electrical leads. Medical leads deliver electrical energy for stimulation of tissue, receive sensed electrical impulses from tissue, or transfer other sensory data indicative of a physical parameter. For example, implantable cardiac pacemakers, cardioverters, or defibrillators commonly have one or more leads connecting the device to cardiac tissue. The leads are typically inserted through a vein and guided into the target location of the cardiac tissue. Once so located, the distal end of the lead is typically affixed to the tissue to secure the lead in the desired location.

Maintaining a sterile field around the incision site is especially important during the implantation procedure. The sterile field prevents contamination that may otherwise occur due to unsanitary conditions. Contamination of the surgical incision site during the implant procedure can lead to pocket infection (infection of the incision site) which may propagate to the cardiac tissue. Therefore, numerous steps are taken during the implant procedure to minimize or prevent the risk of contamination of the surgical incision site. In addition to providing a sterile field around the incision site, all the instruments, tools and equipment that come in contact with the sterile field during the implant procedure are sterilized prior to use and re-sterilized if any contamination is suspected.

Generally, the lead implant procedure may be thought of as a two-phase process. The first involves the placement of the lead in the target tissue while the second phase involves verification of the implanted lead's functionality and determining whether the placement location is appropriate or if there is a need to reposition the lead. This verification is typically performed though testing performed via a programmer. The programmer used can be a fully functional programmer, such as MEDTRONIC MODEL 9790®, or a task specific programmer, such as a pacing system analyzer. In the first phase, a lead is passed through a vein into the desired tissue location and secured to the tissue. Following the placement of the distal end of the lead in the target tissue, a programmer is attached to the proximal end of the lead and various parameters are checked to verify the functionality and whether the lead implant location is appropriate. Thereafter the implantable medical device is connected to the lead and the incision site is closed thereby sealing the implantable medical device and lead within the patient's body.

As the foregoing discussion of the implant procedure demonstrates, the need to re-position the distal end of the lead is typically discovered during the second phase and after much time has been expended placing the lead in the first phase. Moreover, the programmer is located outside the sterile field and is connected to the leads using a set of cables.

The programmer cables therefore have to be sterilized and care taken to ensure that they remain within the sterile field during the implant procedure to prevent contamination of the incision site. Furthermore, the process of re-positioning the lead to an optimal location requires that the programmer cable be disconnected from the lead to allow for the lead to be navigated to the new location in the tissue. As such, many implant procedures may be cumbersome and time consuming.

BRIEF SUMMARY OF DISCLOSURE

The illustrative implementations of the present disclosure include lead coupling devices having electrical connectivity to a lead so as to facilitate improved implant procedure speed and reduce the risk of infection.

In one embodiment a pulse generator, a power source, and electrical contacts are integrated into a housing assembly to provide a lead coupling device. The device includes a channel which is adapted to receive a lead. Further, the electrical contacts are disposed on the exterior surface of the channel of the device to provide electrical connectivity between the lead and the device.

In another embodiment the lead coupling device further includes a wireless communication module that provides wireless communication between the device and an external device. The device eliminates the need for a physical wired connection between the lead and the external device while enabling real time measurements to be performed through the lead during the implant procedure.

In yet another embodiment, a display is coupled to the lead coupling device to provide an indication of a parameter sensed through the lead. The sensed parameter in one embodiment is the impedance of tissue adjacent to the lead.

In another embodiment, a lead coupling device includes means for engaging a proximal end of a lead, means for electrically coupling the lead, and means for receiving a signal sensed by the lead.

In another embodiment, a method of implanting a lead comprises connecting a lead to a lead coupling device such that the lead may be maneuvered during implantation, providing electrical energy to the lead and receiving a sensed signal from the lead.

The foregoing summary is intended to briefly introduce the reader to the basic concepts of the present disclosure and should not be construed as limiting. The details of one or more embodiments are set forth in the accompanying drawings and the description below. In the drawings, like numerals are used to denote identical elements. Other features, objects, and advantages of these embodiments will be apparent from the description and drawings, and from the claims.

DETAILED DESCRIPTION

Figure 1:
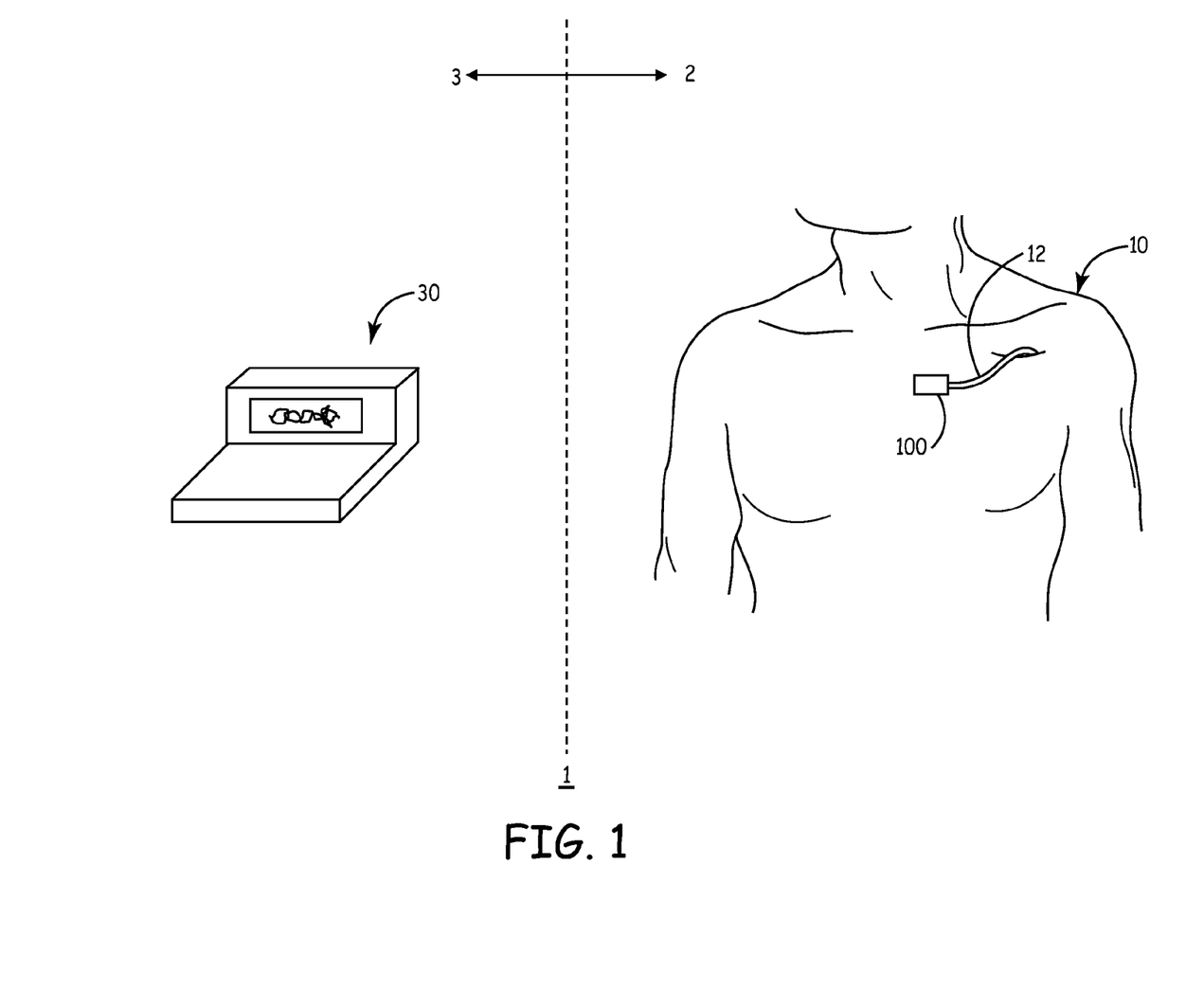
FIG. 1 is a schematic overview of a system with a coupling device coupled to an electrical lead for an implant procedure.

FIG. 1 is a schematic overview of exemplary system which depicts a sterile field 2 and a non-sterile field 3 during an implant procedure of medical electrical lead 12 into a patient 10. Ordinarily, an electrical connector assembly disposed on lead 12 is coupled to a programmer 30 through a programmer cable (not shown) that extends from the non-sterile field 3 to the sterile field 2. Consequentially, encroachment of the sterile field 2 occurs every time the cables are clipped on and off the lead 12 during the implant procedure.

In order to reduce contamination of the sterile field 2, a lead coupling device 100 that couples directly to the lead 12 is provided. In one embodiment, the coupling device 100 incorporates a wireless communication protocol that enables communication with external devices such as the programmer 30. With the wireless communication capability, the coupling device 100 may remain connected to the lead 12 during the entire implant procedure while permitting any desired communication with programmer 30 located outside the sterile field 2.

Figure 2:
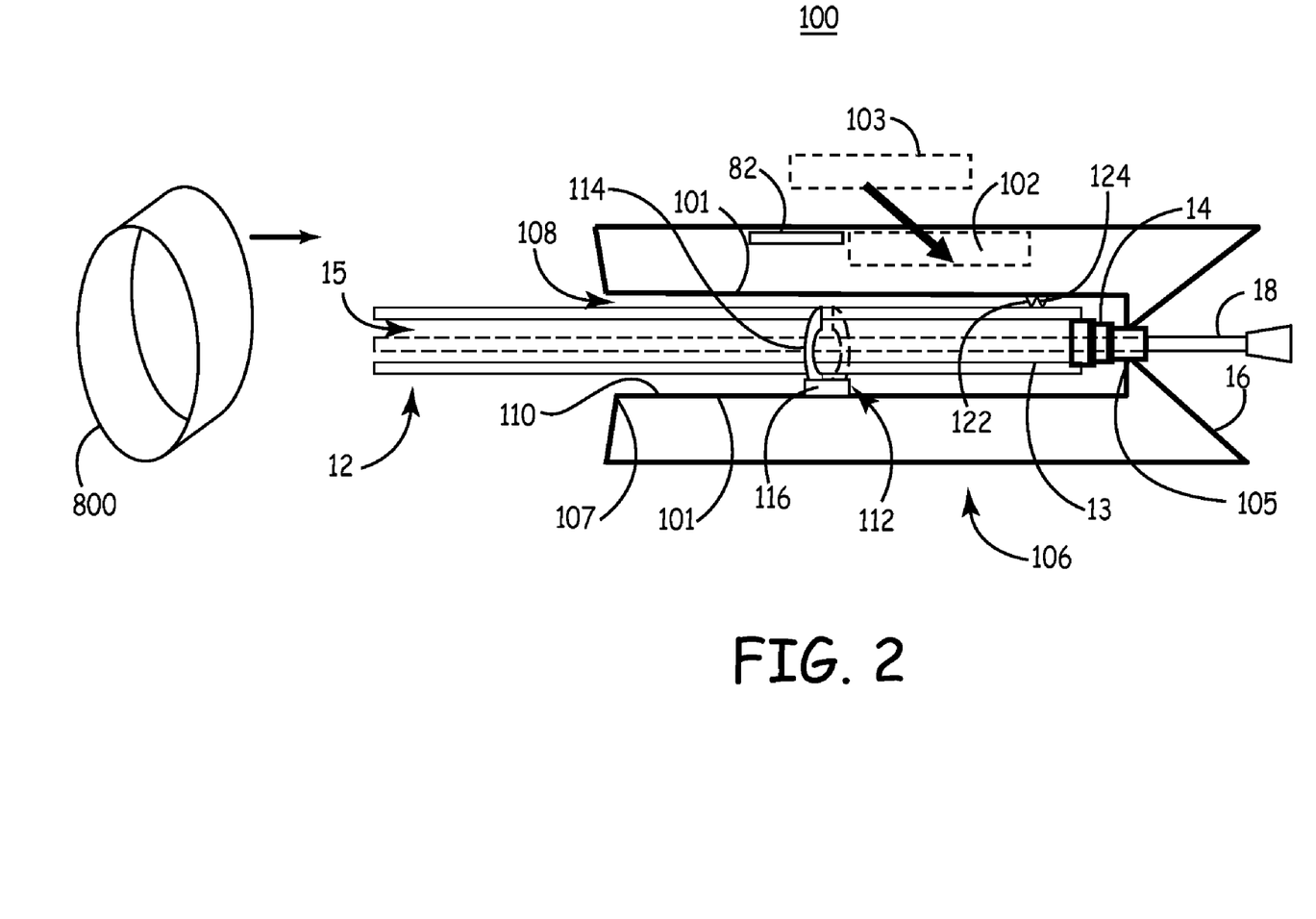
FIG. 2 is a side sectional view of the coupling device coupled to an electrical lead.

FIG. 2 is a side sectional view of a coupling device 100 coupled to lead 12. The lead 12 includes a connector pin 14 at a proximal end 13 of lead 12 and an opening (not shown) that extends to lumen 15. It may be noted that the lead 12 is merely exemplary, and many other lead configurations may be employed with the present disclosure. The coupling device 100 includes a housing 106 with electronic components (FIG. 4) disposed within the housing 106. The housing 106 can be fabricated from any suitable material, including plastic or metal, that can be properly sterilized for use in a surgical field. In an exemplary embodiment, housing 106 is formed from a molding fabrication process. The molding process includes mounting the electronic components on an inner layer 101 of a plastic material and subsequently coating the electronics through an overmold process. Alternatively, the housing 106 may be formed with an electronics component chamber 102, having a cover 103 that provides access to the electronic components.

The outer surface of housing 106 may include a gripping or textured surface (e.g., ridges) to facilitate handling of the coupling device 100. In alternate embodiments, a sleeve 800 may be provided for placement over the housing 106 to facilitate gripping.

A lead channel 108 is disposed within the housing 106 to receive the proximal portion 13 of lead 12. The lead channel 108 extends from a distal opening 107 to a proximal opening 105 and guides the lead 12 toward the proximal end of the coupling device 100. In one embodiment, the size of the proximal opening 105 and distal opening 107 is selected to be larger than the diameter of lead 12.

In some embodiments, a guide tool 18, such as a stylet or a guidewire, designed to facilitate maneuvering of the lead 12 is inserted through the lumen 15. The tool 18 provides additional rigidity to lead 12 and facilitates navigation. However, due to the small diameter of certain of the lead 12 configurations, the lumen is similarly small. To facilitate the insertion of the tool 18 into the lumen 15, the distal opening 107 is provided with a tapered portion 16. The tapered portion 16 provides an enlarged opening that facilitates the insertion of tool 18 into the lumen 15.

An optional lead engagement mechanism 112 may be provided to facilitate gripping of the lead 12. Functionally, the engagement mechanism acts to grip the body of lead 12 so that torque can be applied to the lead 12 by rotating the coupling device 100. Alternatively, the lead channel 108 alone, or in combination with the engagement mechanism 112 can be configured to grip the lead 12 through a frictional fit. As used herein, gripping includes but is not limited to clamping, squeezing, locking, sliding, compressing, screwing, twisting, snapping, interlocking, or otherwise causing appropriate engagement between the lead 12 and the coupling device 100.

In the embodiment illustrated in FIG. 2, engagement mechanism 112 is a resilient member having a C-shaped clamp 114 affixed to a base 116 and medially disposed within the lead channel 108. The clamp 114 is resilient or spring biased so that insertion of the lead 12 causes the clamp 114 to expand and generate an interference fit. Alternatively, other shapes, prong or clamp configurations could be employed. The C-shaped clamp 114 or equivalent interference fit arrangements do not require additional actions to be taken by the implanting physician beyond insertion of the lead 12 into the coupling device 100. Alternative active clamping mechanisms may be used that provide additional gripping force, but do require additional steps in their use along with additional components. The particular configuration selected will depend upon the leads being implanted and the active fixation requirements of those leads.

In general, the force required to insert the lead 12 into the lead channel 108 will depend upon the mechanism employed to grip the lead 12. For example, the resilient clamp 114 will require sufficient force to overcome the spring tension or resiliency of the clamp 114. A lead channel 108 providing a frictional lock will require sufficient force to overcome the frictional forces. With an active external clamping mechanism, seating the lead 12 would require little applied force, as the gripping force is selectively applied after insertion. Nonetheless, it is desirable for the lead 12 to be insertable into the lead channel 108 with as minimal force as possible. By way of example, but not limitation, the mechanism employed may be configured such that only a minimal force ranging from 1.5 lbs to 2.5 lbs would be required to insert the lead 12 into the lead channel 108.

Figure 3:
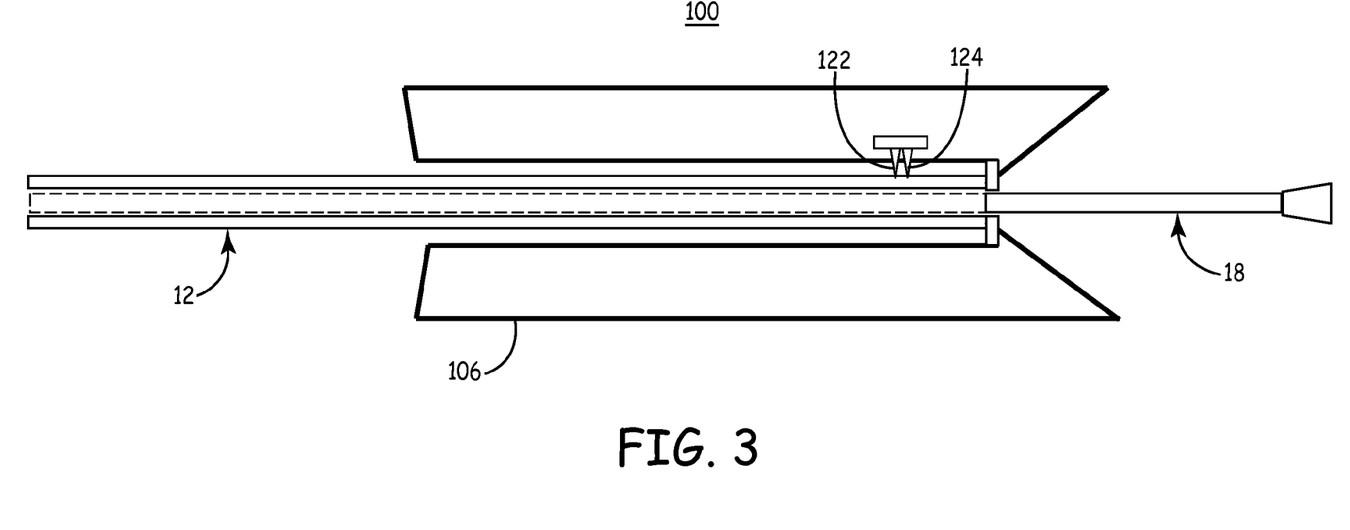
FIG. 3 is a side sectional view of the coupling device including electrical contacts.

As illustrated in FIG. 3, electrical contacts 122, 124 are positioned in the lead channel 108 such that a portion of their conducting surface is exposed. The exposed portions of electrical contacts 122, 124 are configured to engage the electrical connector assembly (not shown) of the lead 108. In one embodiment, the two-contact electrical arrangement electrically and mechanically couples the coupling device 100 to lead 12 having an IS-1 standard connector assembly. In alternate embodiments of the present disclosure, additional electrical contacts may be provided on coupling device 100 so as to correspond to any other connector assembly standard that is used for lead 12. For instance, coupling device 100 is provided with an electrical contact arrangement that corresponds to a DF-1 connector standard, or a four contact arrangement to couple lead 12 with a connector assembly conforming to an IS-4 connector standard.

The contacts 122, 124 are coupled to the electrical circuitry (FIG. 4) disposed within the housing 106. In the illustrated embodiment, the contacts 122, 124 are formed as spring contacts. However, the electrical contacts 122, 124 could take other forms such as a set screw rotated from the outer surface 104 to engage the lead connector assembly (not shown). To facilitate electrical conduction between the lead 12 and the coupling device 100, the electrical contacts 122, 124 are formed from a noble material such as platinum or gold.

Figure 4:
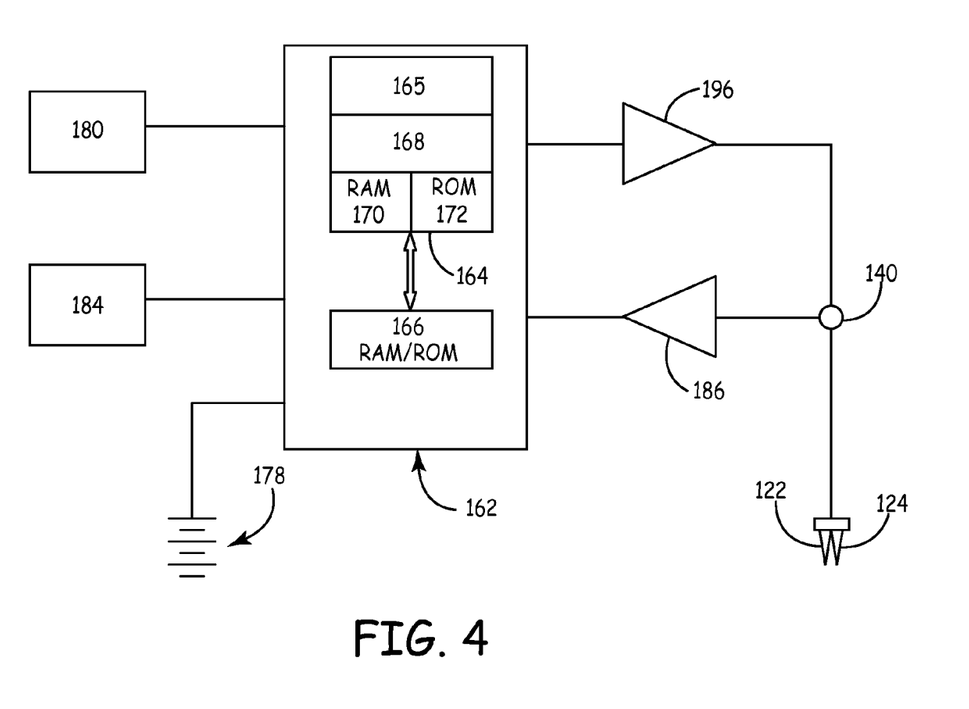
FIG. 4 is a functional block diagram illustrating various constituent electrical components of a coupling device.

FIG. 4 is a functional block diagram illustrating various electrical components of the coupling device 100 that includes a microprocessor-based architecture. The electrical contacts 122, 124 are functionally coupled to a pulse generator 196 via node 140. Pulse generator 196 is coupled to microcomputer circuit 162 which is used to control and/or monitor generation of electrical energy by the pulse generator 196 using software-implemented algorithms stored therein. Microcomputer circuit 162 comprises on-board circuit 164 and off-board circuit 166. On-board circuit 164 includes microprocessor 165, system clock circuit 168 and on-board RAM 170 and ROM 172. Off-board circuit 166 comprises a RAM/ROM unit. A multiplexer unit 184 is optionally coupled to microcomputer 162 to allow selectivity of anode and cathode arrangements of the electrical connector on lead 12.

Electrical energy generated by the pulse generator 196 is transmitted through node 140 and this energy is provided to the lead 12 through electrical contacts 122, 124. In one embodiment, microcomputer circuit 162 controls the amplitude and duration of the electrical energy generated by the pulse generator 196.

Continuing to refer to FIG. 4, sensing circuitry 186 is coupled to the microcomputer circuit 162 to receive one or more signals that is sensed via a sensor (not shown) or electrode (not shown) on lead 12. The sensed signals are transmitted through the lead 12 and provided to the coupling device 100 through electrical contacts 122, 124. The sensed signal received at electrical contacts 122, 124 is transmitted through node 140 and provided to the sensing circuitry 186. The microcomputer circuit 162 includes software-implemented algorithms to control the sensing operation of the coupling device 100. The sensed signals received by the sensing circuitry 186 include, for example, physiological signal such as impedance, voltage, current, temperature, heart rate, blood pressure, electromyography, electro-encephalography, and electro-oculography.

In additional embodiments, coupling device 100 is configured for wireless communication with an external programming unit 30 (FIG. 1). Therefore, a wireless communication module 180 is coupled to the microcomputer circuit 162 to provide the wireless communication. Any of a number of suitable programming and wireless communication protocols known in the art may be employed so long as the desired information is transmitted to and from the coupling device 100. In alternative embodiments of the present disclosure, other communication protocols such as Bluetooth® communication, IEEE 802.11, Home RF or other short-and long-range wireless protocols may be employed as the wireless communication technique.

The external programming unit 30 (FIG. 1) may be used in conjunction with or as a substitute to the software implemented algorithms in microcomputer circuit 162 to control the operation of coupling device 100. In other words, the pulse generator 196 provides electrical energy to lead 12 based on a command received from the microcomputer 162 or a command sent from external programming unit 30. Similarly, the sensing operation by sensing circuitry 186 may be initiated by the microcomputer 162 or the external programming unit 30. Further, the wireless communication module 180 provides wireless transfer of sensed data received by the coupling device 100 to the external programming unit 30. It is generally preferred that the particular programming and communication protocol selected permit the entry and storage of multiple physiological parameters. However, in some embodiments of the present disclosure, the protocol chosen could be a "repeating" protocol where the sensed parameters are merely relayed to the programming unit 30 (FIG. 1) without the need for storage.

In some embodiments, security features are incorporated into the wireless communication protocol utilized to prevent cross-talk between various devices. Exemplary embodiments of the security features of the present disclosure could include algorithms within the programmer 30 or the coupling device 100 that initiate a communication session. The algorithms incorporate unique device identification of the coupling device 100. Thus prior to initiating the communication session between the programmer 30 and the coupling device 100, the identity of the coupling device 100 is authenticated by the programmer 30. Other security features known in the art may be utilized for the security function.

The electrical components shown in FIG. 4 are powered by a battery power source 178 in accordance with common practice in the art. Such a power source could either be rechargeable or non-rechargeable.

As discussed above, implantable lead 12 varies in construction, size, and design depending on the model of the lead 12. In addition to the variations noted, some of the available leads 12 include a helical coil (not shown) at the distal tip of the lead 12. This helical coil is typically rotated into the target tissue to affix the lead 12 into the tissue. The helical coil is coupled to a conductor that extends from the distal end (not shown) to the proximal end 13 of the lead 12 and terminates at a pin 14. Subsequent to implantation of the lead 12, pin 14 is coupled to an electrical connector of a medical device (not shown) to be implanted in the patient 10. The implantation procedure of lead 12 having a helical coil therefore requires the rotation of the pin 14 which causes rotation of the helical coil in order to secure the helical coil into the target tissue.

Figure 5:
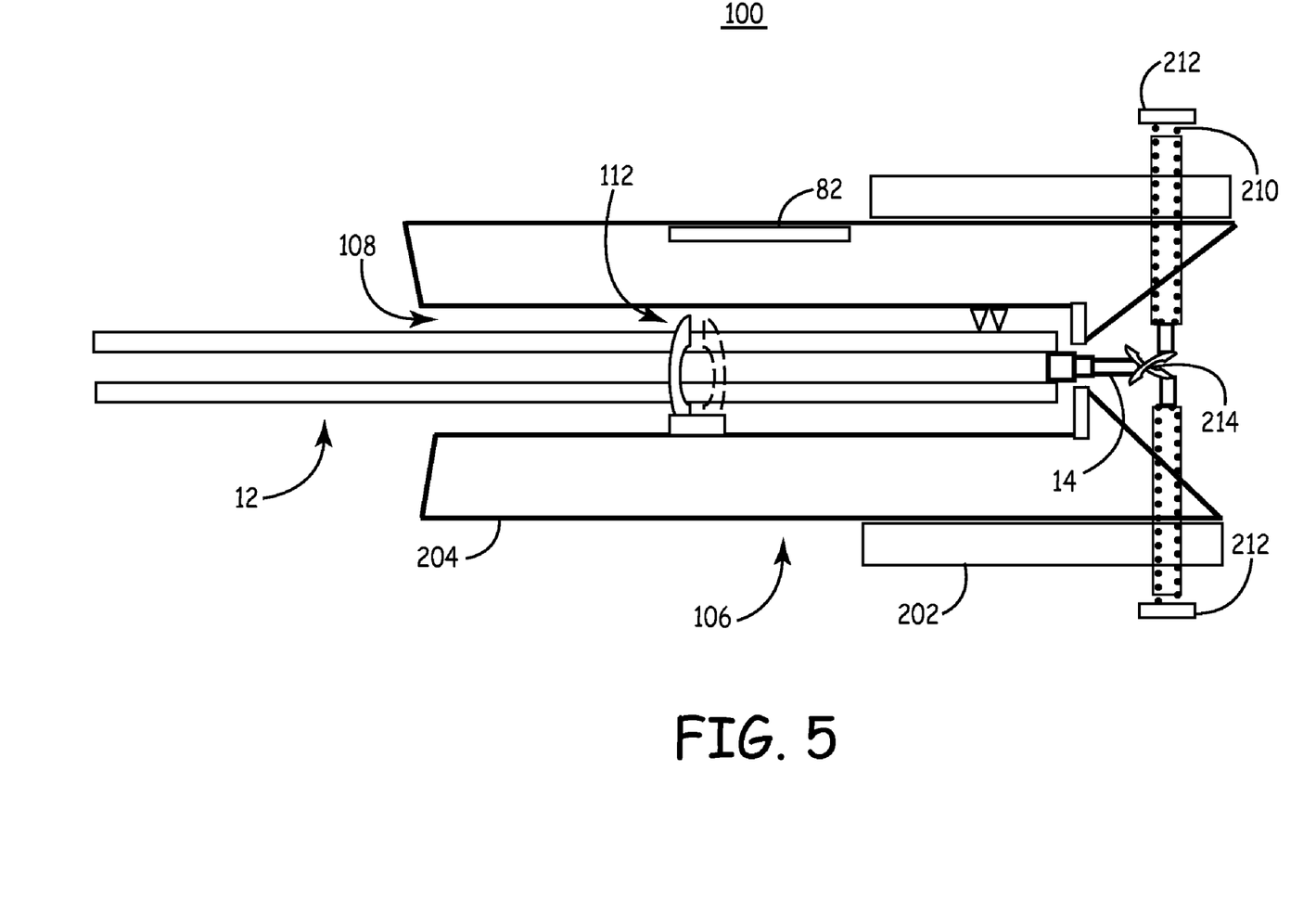
FIG. 5 depicts a side sectional view of an alternative coupling device.

Turning now to FIG. 5, an alternative embodiment of the coupling device of FIG. 2 is depicted. The coupling device 100 includes a proximal portion 202 and a distal portion 204 that form a housing 106. The proximal portion 202 and the distal portion 204 may be formed as an integral housing to provide a rigid coupling device 100. In other embodiments, the proximal portion 202 and distal portions 204 are formed separately and interconnected to form the housing 106. The proximal portion 202 and distal portion 204 are formed to permit relative rotation about one another. Housing 106 may be formed of a plastic, metal or any other material that can be properly sterilized for use in a surgical field. Any of the fabrication processes described above with respect to FIG. 2 may be used in the fabrication of the housing 106 illustrated in the embodiment of FIG. 5.

In the exemplary illustration of FIG. 5, an engagement mechanism 112 (described with respect to FIG. 2) is located within the distal portion 204 of lead channel 108 to permit gripping of a lead. This view also shows a gripping mechanism 214 designed to grip the connector pin 14. Any gripping mechanism know in the art could be used to grip the pin 14. The exemplary mechanism 214 is a hand actuated spring-clip 210 that employs the use of an actuating member 212 on the exterior surface of the proximal portion 202. Functionally, the actuating member 212 is compressed to expand a gripping surface of the gripping mechanism 214 so as to position the pin 14 there-between or release the pin 14. Conversely, releasing the compressing force exerted on the actuating member 212 causes the gripping surface to contract thereby engaging the pin 14.

The coupling devices 100 of FIGS. 2 and 5 optionally include a display 82 located on an outer surface of the device 100. Displaying an indication of the sensed parameter either on the coupling device 100 or on the programmer 30 is beneficial to the implanting procedure. Real time display of the sensed parameters, as the lead 12 is navigated through the patient 10 will, for example, facilitate the optimization of the implant location within the target tissue. As previously described, any of the aforementioned parameters may be sensed. In one embodiment the sensed signal is displayed as a "raw" number; in other words, the plain sensed parameter is displayed without further action. In other embodiments, the sensed parameter is processed by microcomputer 162 to derive an indication that serves as a direct feedback to the implanting physician.

One example of a parameter that may be sensed and displayed, with or without, processing is impedance. The electrodes on lead 12 could be utilized to perform impedance measurements of the surrounding tissue or fluid as the lead 12 is progressively inserted into patient 10. The typical impedance value of blood is usually about 600 ohms while body tissue will range from about 800 ohms to over 1400 ohms. The variation of the body tissue impedance will depend on the amount of fluid in the tissue. Tissue with a normal amount of fluid is generally about 1000 ohms. Accordingly as the lead 12 is navigated through the vein (blood) into the target tissue, the impedance value will increase from about 600 ohms to 1000 ohms. This abrupt change in impedance measurement serves as an indicator to the implanting physician that lead 12 is currently in contact with tissue. The raw impedance values may be displayed and the physician may correlate the measure value with the surrounding matter e.g., plain blood, tissue with minimal fluid. Alternatively, the impedance values may be processed according to various criteria within the microprocessor 162, and an indication of the particular matter within which the lead 12 is in contact displayed.

Additionally, the aforementioned helical coil located on lead 12 is typically rotated to secure the lead tip in the tissue. One issue that may arise with rotation of the helical coil is over-rotation that may result in damage to the tissue. It may be noted that the impedance of tissue will vary depending on the amount of fluid in the tissue. Hence, aided with display 82 and impedance processing on microcomputer 162 on certain embodiments of coupling device 100, impedance measurements may be performed to facilitate the determination of when the helical coil is sufficiently rotated. As the rotation of the helical coil is performed, fluid is squeezed out of the tissue and the impedance measurement consequentially increases serving as an indication that the lead tip is successfully lodged in the tissue such that further rotation is not necessary. Moreover, because over-rotation may cause tissue damage, further rotation of the helical coil will allow blood to re-enter the fixation site and consequentially the impedance value drops. The impedance measurements performed during the rotation are displayed in real-time as the rotation occurs. Changes in impedance measurements serve as an indicator of the amount of fluid displaced from the tissue and these measurements are indicative of the portion of the helical coil that is embedded into the tissue. Thus measuring the impedance value of the tissue as the helical coil is rotated facilitates the prevention of over-rotation of the lead and thus minimizes or reduces tissue damage.

Furthermore, the coupling device 100 may determine whether the implant location is optimal by sensing or receiving an indication of an unintended consequence. One example is phrenic nerve stimulation which may occur with a left ventricular (LV) lead since the LV lead is often implanted proximate this nerve. Either due to position or due to elevated levels for stimulation therapy, the phrenic nerve might be stimulated by the LV lead. Thus by delivering electrical energy stimulation concurrently during the implant procedure, the implanting physician may be able to identify an appropriate placement position based on the stimulation levels required for the intended therapy.

As mentioned the alternative embodiments of coupling device 100 illustrated in FIGS. 2 and 5 can be fabricated from any suitable material, including plastic or metal that can be properly sterilized for use in a surgical field. Some examples of sterilizing techniques are the use of flash steam (thus the material would need to be able to withstand high temperature) or sterilizing chemicals such as Ethylene Oxide (hence the material would need to be compatible with the chemical) or nitrogen gas (similarly the material would need to be compatible with the gas). In yet other alternative embodiments, the coupling device 100 includes a polymer layer that is disposed over the housing for ease of cleaning and sterilization such as epoxy or polyester.

Figure 6A:
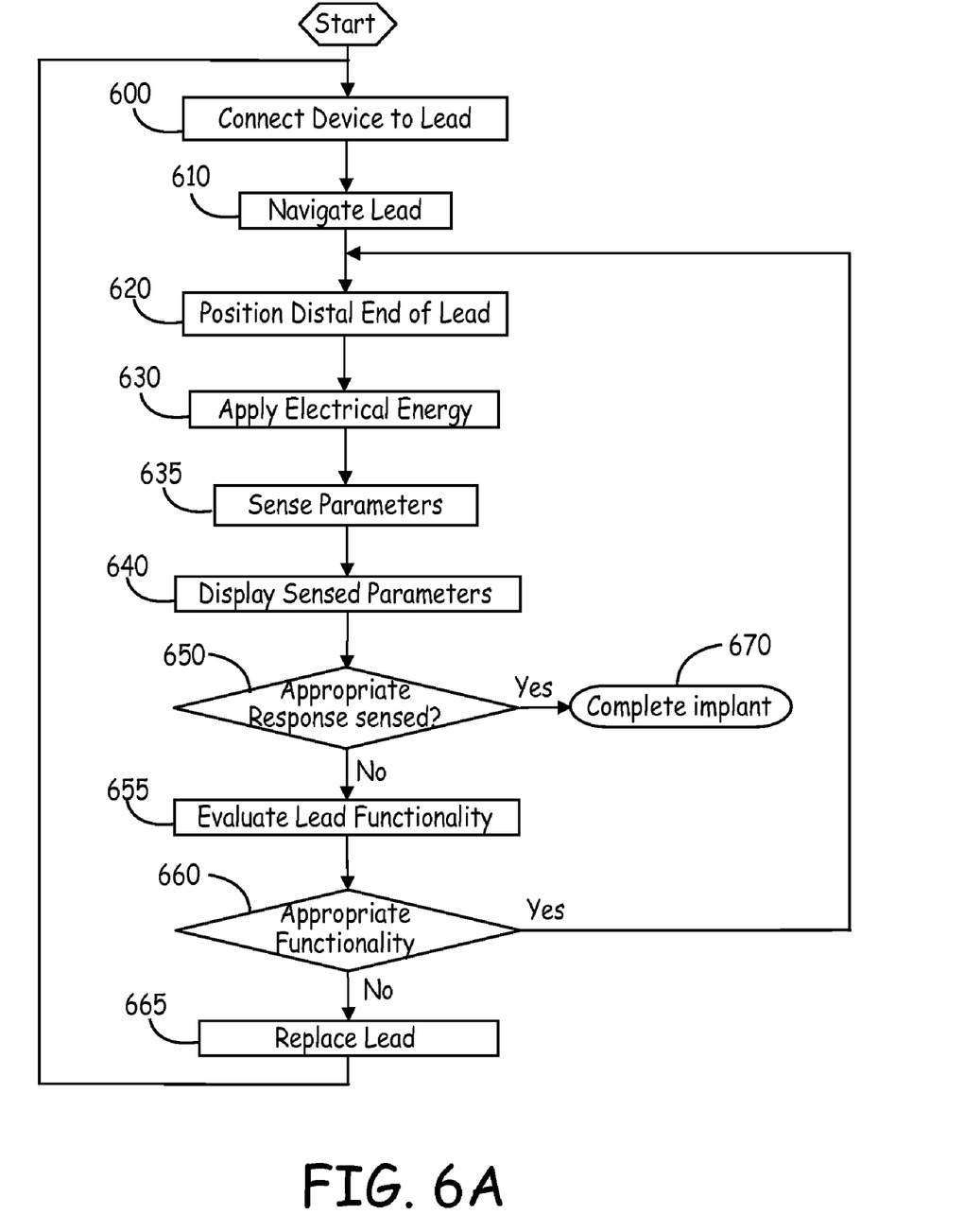
FIGS. 6A and 6B are functional flowcharts of the operation of the coupling devices of FIGS. 2 and 5.

FIGS. 6A is a functional flowchart illustrating the over-all stand-alone operation of the coupling devices of FIGS. 2 and 5 in conjunction with a lead. At 600, the lead 12 is connected to the coupling device 100 by inserting the proximal end 13 of the lead 12 through the distal opening 107 of the coupling device 100 and advancing the lead 12 through the lead receiving channel 108 toward the proximal opening 105 of the coupling device 100. The electrical connector assembly of the lead is aligned with the electrical contacts 122, 124 of the coupling device 100 so as to be in contact.

Next, the implanting physician makes a determination of whether it is desired to use the coupling device 100 to navigate 610 the lead 12. If desired, the body of the lead 12 is securely coupled to the coupling device 100 using any implementations of the engagement mechanisms 112 described above. Additionally, in alternative implementations having a pin gripping mechanism 214, the physician decides whether to use the coupling device 100 for rotation of the pin. If desired, the lead pin 14 may be securely coupled to the coupling device 100. Further, the implanting physician determines whether to use a guiding tool 18 to navigate the lead 12 and selects the desired tool 18. The tool 18 is inserted into the lumen 15 of the lead 12.

At 610, the implanting physician then proceeds to navigate the lead 12 through the patient 10 to the desired tissue location. Once the lead 12 is advanced into the general area where it is desired to affix the lead 12, the physician positions 620 the distal end of the lead 12 against the tissue. The coupling device 100 is activated to provide electrical energy 630 to the tissue through the lead 12. In alternate embodiments, providing electrical energy from the coupling device 100 is also performed during the process of navigation of the lead 12.

Additionally, the physician may activate the coupling device 100 at 635 to sense one or more parameters described above through the lead 12. In one embodiment, the sensed parameters are displayed 640 on the display 82 included on the coupling device 100. The sensed parameters are used at 650 to derive an indication of whether the implant location is appropriate or to verify if capture has occurred.

If the displayed parameters do not indicate that a desired response is achieved, the lead functionality is evaluated 655. In one embodiment, the evaluation 660 of lead functionality is performed through providing electrical energy to the lead 12 and determining if the energy is conducted to the distal end by observing tissue response. Alternatively, the coupling device 100 initiates sensing of various parameters via the lead 12, and the sensed parameters received by the device are evaluated 660 to determine lead functionality. If it is determined that the functionality of the lead is inappropriate, the lead 12 is replaced at 665. Otherwise, the physician re-positions the lead 12 at 620 and repeats the above steps until an appropriate response is achieved. Upon achieving a desirable response, the coupling device 100 is disconnected and the implant procedure is completed 670 by connecting the implantable medical device and closing the incision site.

Figure 6B:
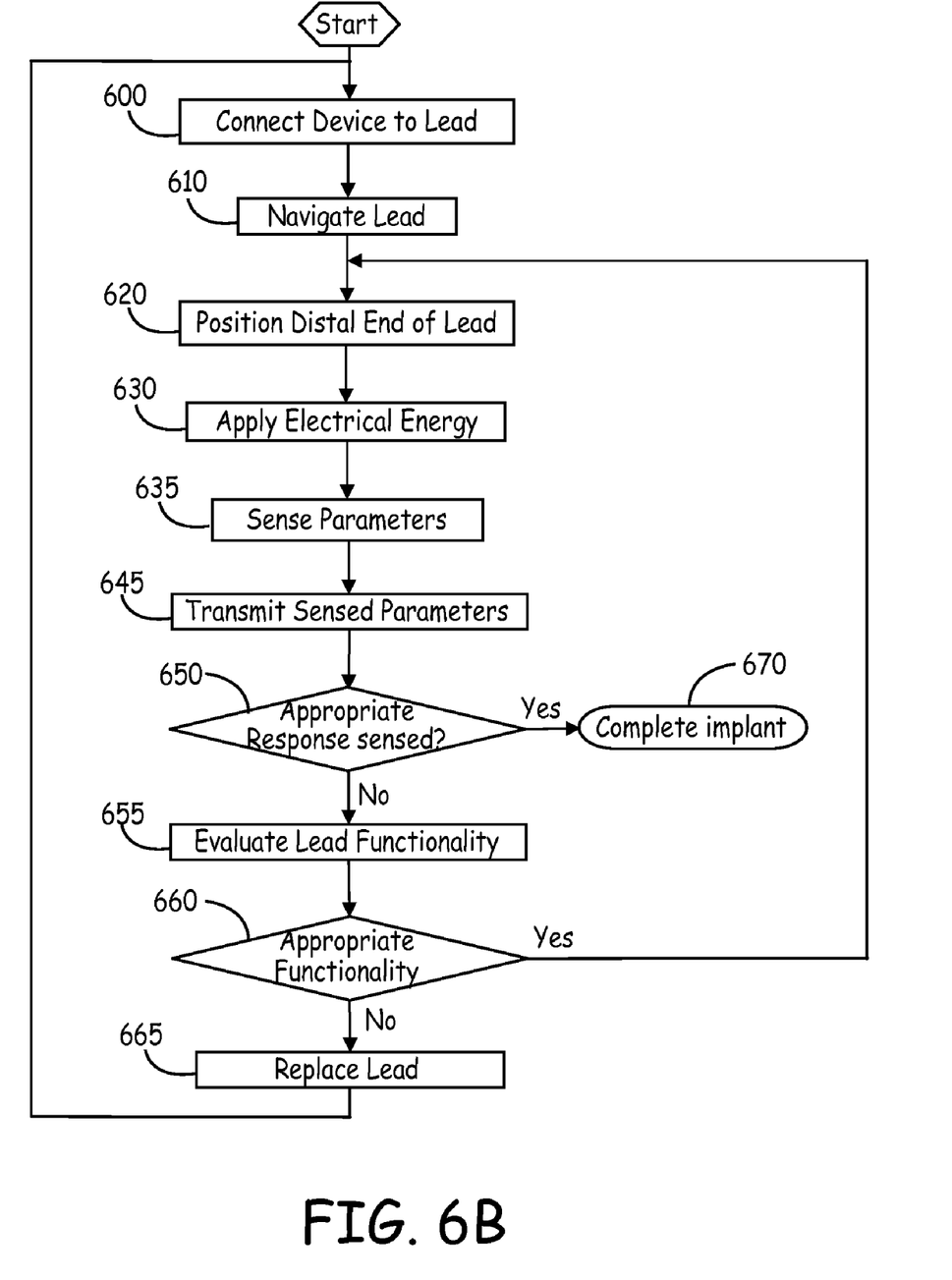

FIG. 6B is a functional flowchart illustrating an alternative over-all operation of the coupling devices 100 of FIGS. 2 and 5 in conjunction with a lead 12 whereby the coupling devices 100 have wireless communication capability. In the alternate embodiment, the coupling device 100 is in communication with an external device 30, such as a programmer. Thus the operation to provide electrical energy 630 is alternatively initiated from an external device 30 that is in communication with the coupling device 100. Similarly, the operation to sense one or more parameters 635 is alternatively initiated from the external device 30. It will be noted that the sensed parameters may alternatively, or additionally, be displayed at an external display 30 such as that available on the external device 30. Thus at 645, the sensed parameters may be transmitted to the external device 30 and subsequently displayed, if desired.

Although the present disclosure has been described according to specific embodiments, it is recognized that with the benefit of this disclosure, one of ordinary skill in the art may conceive variations of these embodiments that generally gain the benefits provided by a remote lead coupling device. The above described embodiments should therefore not be considered limiting in regard to the following claims.

The invention claimed is:

1. A lead coupling device, comprising:
 a housing having a proximal opening at a proximal end and a distal opening at a distal end;
 a lead receiving channel disposed within the housing and extending from the proximal opening to the distal opening, wherein said channel is adapted to receive a medical lead;
 a lead guiding tool receiving mechanism disposed on the housing;
 a pulse generator disposed within the housing for providing electrical energy;
 a processor coupled to the pulse generator;
 at least one electrical contact mounted within the channel and coupled to the pulse generator, wherein a portion of the contact is adapted to contact the lead; and
 a power source disposed within the housing and coupled to the pulse generator; and
 wherein the housing further includes a proximal section and a distal section that are rotatably coupled so that relative rotation is permitted between the proximal section and the distal section; and wherein the proximal section comprises a pin gripping mechanism configured to engage a pin of the lead.

2. The lead coupling device of claim 1, further comprising sensing circuitry coupled to the processor, wherein the sensing circuitry is configured to receive a physiological parameter sensed by the lead.

3. The lead coupling device of claim 2, wherein the sensed physiological parameter is processed to give an indication of a medium surrounding an electrode on the lead tip.

4. The lead coupling device of claim 2, wherein the sensed physiological parameter is impedance.

5. The lead coupling device of claim 1, further comprising a lead engagement mechanism configured to engage the lead.

6. The lead coupling device of claim 1, further comprising a wireless communication module.

7. The lead coupling device of claim 6, wherein the wireless communication module includes at least one of a communication protocol comprising distant telemetry, Bluetooth™, IEEE 802.11.

8. The lead coupling device of claim 1, further comprising a display.

9. The lead coupling device of claim 1, wherein the outer surface of the housing has a textured surface configured for gripping.

10. A lead coupling device, comprising:
 a housing having a proximal opening at a proximal end and a distal opening at a distal end;
 means for receiving a medical lead disposed within the housing;
 means for receiving a lead guiding tool disposed on the housing;
 means for generating electrical energy disposed within the housing;
 pulse generating means coupled to the means for generating electrical energy; and
 means for electrically coupling the lead coupled to the pulse generating means; and
 wherein the housing further includes a proximal section and a distal section that are rotatably coupled so that relative rotation is permitted between the proximal section and the distal section; and wherein the proximal section comprises means for gripping a pin configured to engage a pin of the lead.

11. The lead coupling device of claim 10, further comprising means for sensing, wherein the sensing means is configured to receive a physiological signal sensed by the lead.

12. The lead coupling device of claim 11, further comprising means for processing the sensed signal to derive an indication of the medium surrounding an electrode on the lead.

13. The lead coupling device of claim 12, further comprising means for displaying the processed signal.

14. The lead coupling device of claim 10, further comprising means for engaging the lead.

* * * * *